(12) United States Patent
Edberg

(10) Patent No.: US 6,626,942 B1
(45) Date of Patent: Sep. 30, 2003

(54) IMPLANT FOR IMPLANTATION IN HUMANS OR ANIMALS COMPRISING FLEXIBLE THREAD-SHAPED ELEMENTS

(75) Inventor: Bengt Edberg, Göteborg (SE)

(73) Assignee: Artimplant AB (SE)

( * ) Notice: Subject to any disclaimer, the term of this patent is extended or adjusted under 35 U.S.C. 154(b) by 0 days.

(21) Appl. No.: 09/868,055

(22) PCT Filed: Nov. 25, 1999

(86) PCT No.: PCT/SE99/02185
§ 371 (c)(1),
(2), (4) Date: Jun. 13, 2001

(87) PCT Pub. No.: WO00/35507
PCT Pub. Date: Jun. 22, 2000

(30) Foreign Application Priority Data

Dec. 15, 1998 (SE) .............................................. 9804321

(51) Int. Cl.$^7$ .................................................. A61F 2/08
(52) U.S. Cl. .................................. 623/13.18; 623/13.2
(58) Field of Search .......................... 623/13.11, 13.12, 623/13.13, 13.14, 13.15, 13.16, 13.17, 13.18, 13.19, 13.2

(56) References Cited

U.S. PATENT DOCUMENTS

| | | | | |
|---|---|---|---|---|
| 4,792,336 A | * | 12/1988 | Hlavacek et al. | 623/13.18 |
| 4,834,755 A | * | 5/1989 | Silvestrini et al. | 623/13.19 |
| 4,883,486 A | * | 11/1989 | Kapadia et al. | 623/13.15 |
| 4,987,665 A | * | 1/1991 | Dumican et al. | 28/218 |
| 5,004,474 A | * | 4/1991 | Fronk et al. | 623/13.14 |
| 5,116,372 A | * | 5/1992 | Laboureau | 623/13 |
| 5,192,332 A | * | 3/1993 | Lang et al. | 8/405 |
| 5,217,495 A | * | 6/1993 | Kaplan et al. | 623/13.18 |
| 5,263,984 A | * | 11/1993 | Li et al. | 623/13.18 |
| 5,425,766 A | * | 6/1995 | Bowald | 623/13.18 |
| 5,711,960 A | * | 1/1998 | Shikinami | 424/426 |
| 5,800,543 A | * | 9/1998 | McLeod et al. | 623/13.2 |
| 6,210,441 B1 | * | 4/2001 | Flodin | 623/13.18 |
| 2001/0044659 A1 | * | 11/2001 | Laboureau et al. | 623/13.2 |

FOREIGN PATENT DOCUMENTS

| | | |
|---|---|---|
| SE | 457 692 | 1/1989 |
| SE | 505 703 | 9/1997 |
| WO | 97/22643 | 6/1997 |

* cited by examiner

Primary Examiner—Corrine McDermott
Assistant Examiner—Thomas J Sweet
(74) Attorney, Agent, or Firm—Lerner, David, Littenberg, Krumholz & Mentlik, LLP

(57) ABSTRACT

Biodegradable porous implants are provided which are biocompatible with humans and animals, and which comprise bundles of flexible threads, each of the bundles including a plurality of flexible threads, each of the plurality of flexible threads comprising from 50 to 500 filaments having a combined density of from 5 to 120 tex, each of the bundles having a twist of up to 120 revolutions per meter, and including weft threads holding together the plurality of bundles, the weft threads having a distribution density of up to about 100 threads per cm calculated in the longitudinal direction of the flexible threads.

8 Claims, 1 Drawing Sheet

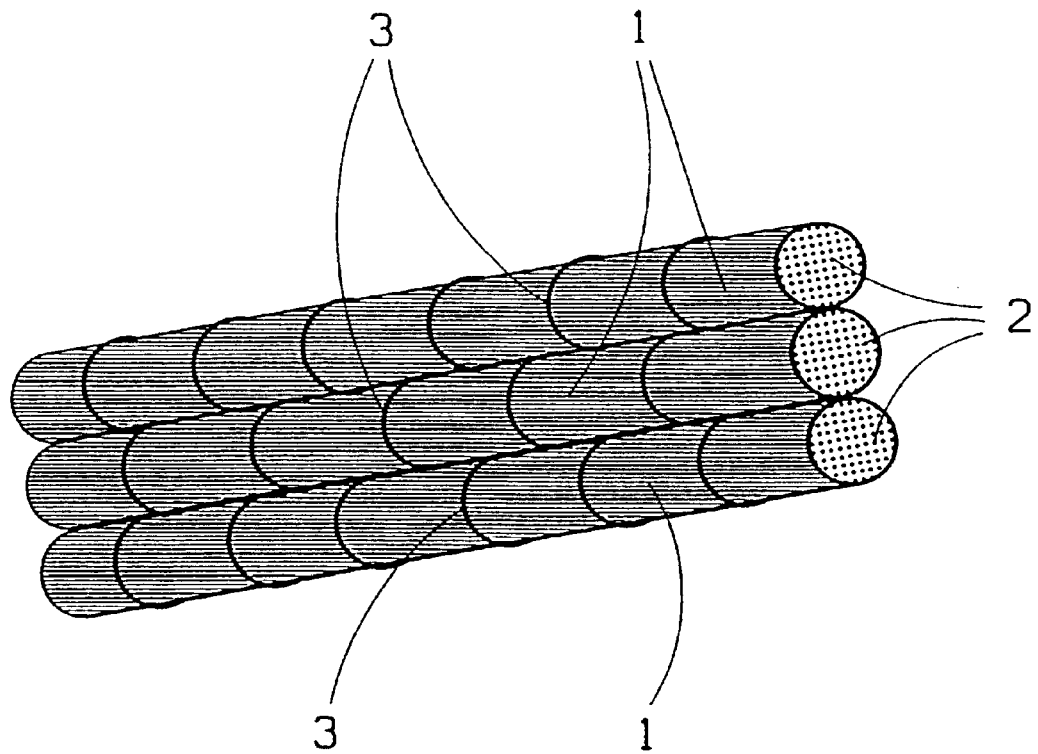
FIG.

IMPLANT FOR IMPLANTATION IN HUMANS OR ANIMALS COMPRISING FLEXIBLE THREAD-SHAPED ELEMENTS

TECHNICAL FIELD

The present invention relates to an implant for implantation in, in particular, humans, which implant comprises flexible, thread-shaped elements and is particularly suitable for replacing ruptured articular ligaments. The implant is intended to be a temporary implant which disintegrates in time into fragments which are so small that they can be transported away by the blood and excreted through the kidneys.

STATE OF THE ART

Every year, millions of people are affected by damage to articular ligaments and tendons. A damaged ligament can be treated by surgical intervention or by conservative therapy. In spite of the fact that leading orthopaedic experts agree that surgical intervention is to be preferred in most cases, conservative therapy remains the most frequently used alternative. A major reason for this is that existing operative techniques using existing implants are considered to be inadequate.

A common feature of all types of reconstruction is that the surgeon has to use some form of replacement material to replace the damaged tissue. The most frequently used type of replacement material is tissue of the patient himself (autograft) which the surgeon takes from other parts of the body. This tissue is often supplemented with a synthetic material as reinforcement (augmentation implant). Alternatively, use is made of only a synthetic material (prosthetic implant). Implant materials which have been tried over the last 20 years in addition to autografts are inter alia tendons from animals (xenografts), deceased humans (allografts), synthetic materials in the form of non-degradable bands (Dacron, polyethylene, polypropylene, carbon fibres, polytetrafluoroethylene), and a degradable band made of polydioxanone.

Temporary implants for implantation in humans or animals comprising flexible, thread-shaped elements are previously known. One such has been described in Swedish patent specification 457692. The implant according to this patent specification consists of a bioresorbable material and is intended to replace completely or partly a tendon, a ligament or a cruciate ligament. The implant has an elongate shape and is flexible. Its main characteristic is that the structure has longitudinal grooves or ducts intended to serve as initial growth guides for new fibrous tissue. Furthermore, a large number of bioresorbable materials are also known and used for other types of implant.

TECHNICAL PROBLEM

In certain cases, the synthetic non-degradable implant materials have proved to have inadequate tissue-affinity and in the majority of cases inadequate elasticity with creep or fatigue failure as a consequence.

Biological tendon tissue from the patient himself, animals or deceased humans has not proved to be an optimum alternative either. The absence of a natural blood supply means that the elasticity and the strength are already reduced after a few weeks. Moreover, there is always a risk of transmitting infection when using implants from other humans and animals. In cases where tissue is taken from other parts of the body, the patient may suffer temporary or permanent harm from the wound created at the place from where healthy tissue has been taken.

SOLUTION

It has therefore long been a requirement to produce a resorbable implant without the abovementioned shortcomings and, according to the following invention, a porous, in humans or animals biodegradable, biocompatible implant for implantation in humans or animals comprising flexible, thread-shaped elements has consequently been produced, which is characterized in that the thread-shaped elements consist of a number of thread bundles containing up to several thousand threads which in turn contain 50 to 500 filaments with a combined density of 5 to 120 tex, the thread bundles having a twist of 0 to 150 revolutions/meter and being held together by weft threads with a distribution density of a few threads per cm up to roughly 100 threads per cm calculated in the longitudinal direction of the thread-shaped element.

According to the invention, it is suitable for the weft threads to consist of the same type of thread as the other threads in the thread-shaped element.

According to the invention, the material in the threads should consist of a linear block polymer with a molecular weight of at least $10^4$ Dalton, preferably at least $10^5$ Dalton, comprising urea groups and urethane groups and also ester groups at such a distance from one another that, after hydrolysis of the same, fragments arise which are so small that they can be excreted from a human body, and also comprising primary $NH_2$-end groups and/or OH-end groups which can be replaced by, for example, monoamines such as butylamine or ethylamine.

The implant according to the invention preferably consists of a central isotropic part for essentially absorbing constant loading, and a movable outer part for absorbing forces caused by extension and/or compression.

According to the invention, the implant consists of an articular ligament implant or tendon implant.

DESCRIPTION OF THE FIGURE

The invention will be described in greater detail below with reference to the appended FIGURE which shows in perspective what an embodiment of the implant according to the present invention looks like.

DETAILED DESCRIPTION

The figure shows a section of an articular ligament according to the present invention comprising only three thread bundles 1. The articular ligament usually consists of, for example, 1 to 500 such thread bundles depending on where in the body it is to be used. As can be seen from the figure, these thread bundles 1 are lightly twisted with a twist of 10 to 150 revolutions per meter. This twist is primarily intended to prevent entanglement of filaments and/or threads across the width of the ligament.

The thread bundles 1 consist of up to several thousand threads 2 which in turn each contain 50 to 500 filaments. Each thread bundle can thus contain a very large number of filaments from a few hundred up to several hundred thousand.

In order for the thread bundles 1 to be held together, they are bound together by weft threads 3 which are preferably applied in a weaving machine and using the simplest possible type of weave, usually plain weave. The distance between the weft threads can vary from a distribution density of a few threads per cm up to roughly 100 threads per cm depending on the desired firmness of the ligament. The closer the threads lie, the more rigid and firm the ligament. The weft threads 3 suitably consist of the same material as the threads 2 in the thread bundles 1.

The thread bundles 2 do not have to have the same thickness throughout the ligament. If the implant is to be used as an articular ligament in a knee, it is suitable for the thread bundles in the central part of the ligament to be made somewhat thicker than the outer parts so that loads across the ligament are as much like the autologous ligament as possible, that is to say with a central isotropic part which is essentially to absorb constant loading while the outer thread bundles can be more easily movable so as to be capable of freely absorbing the forces caused by extension and/or compression which arise, for example, during bending and torsion of a knee joint. The thread bundles can therefore slide somewhat in relation to one another.

The construction according to the invention is loose, which affords an enhanced possibility of immigration of connective tissue cells into the ligament. The strength and the elasticity of the construction can be adapted, which makes it possible for the patient to be active soon after an operation, development of the correct type of collagen fibre thus being stimulated. Adaptation is effected by varying the number of thread bundles, the number of threads in the thread bundles and the density of the weft threads. The strength in an articular ligament according to the present invention can vary between 50 MPa and 500 MPa. The modulus of elasticity in an articular ligament according to the present invention can vary between 100 MPa and 1500 MPa.

The construction according to the present invention affords a number of advantages in comparison with previously known implants, namely maximum utilization of the thread strength as a result of a small filament angle in the fiber strand (small cosine φ factor), and adapted but limited mobility between the fiber strands, a loose construction to enhance the possibility of immigration of the body's own connective tissue cells, and adapted strength and elasticity.

The material in the filaments and the threads should be degradable in the body and preferably consists of those linear block polymers comprising urea groups and urethane groups which comprise hydrolyzable ester groups and are described in Swedish patent specification 505703. Other materials which are degradable and resorbable in the body can also be used.

The invention is not limited to the embodiment described above but can be modified in various ways within the scope of the patent claims.

What is claimed is:

1. Biodegradable porous implants which are biocompatible with humans or animals comprising a plurality of bundles of flexible threads, each of said plurality of bundles comprising a plurality of said flexible threads including a central isotropic portion for absorbing constant loading and a movable outer portion for absorbing forces caused by extension or compression, and each of said plurality of flexible threads comprising from 50 to 500 filaments having a combined density of from 5 to 120 tex, each of said plurality of bundles having a predetermined twist of up to 150 revolutions per meter, and weft thread means holding together said plurality of bundles, said weft thread means having a distribution density of up to about 100 threads per cm calculated in the longitudinal direction of said flexible threads.

2. The biodegradable implants of claim 1 wherein each of said plurality of bundles comprises several thousand of said flexible threads.

3. The biodegradable implants of claim 1 wherein said flexible threads and said weft thread means comprise the same thread material.

4. The biodegradable implants of claim 1 wherein said flexible threads comprise linear block polymers having a molecular weight of at least $10^4$ Dalton, said linear bulk polymers comprising urea groups, urethane groups, and ester groups spaced apart a predetermined distance whereby upon hydrolysis of said flexible threads fragments are produced of a size sufficiently small to be excreted from a human body.

5. The biodegradable implants of claim 4 wherein said linear block polymers have a molecular weight of at least $10^5$ Dalton.

6. The biodegradable implants of claim 4 wherein said linear block polymers include primary $NH_2$-end or OH-end groups replaceable by a monoamine.

7. The biodegradable implants of claim 6 wherein said monoamine comprises butylamine or ethylamine.

8. The biodegradable implants of claim 1 comprising an articular ligament implant or tendon implant.

* * * * *

UNITED STATES PATENT AND TRADEMARK OFFICE
CERTIFICATE OF CORRECTION

PATENT NO. : 6,626,942 B1
DATED : September 30, 2003
INVENTOR(S) : Bengt Edberg

It is certified that error appears in the above-identified patent and that said Letters Patent is hereby corrected as shown below:

Title page,
Item [54], Title, after "FLEXIBLE" insert -- , --.

Delete the specification and substitute therefor the enclosed specification.

Signed and Sealed this

Fifth Day of April, 2005

JON W. DUDAS
*Director of the United States Patent and Trademark Office*

IMPLANT FOR IMPLANTATION IN HUMANS OR ANIMALS COMPRISING FLEXIBLE, THREAD-SHAPED ELEMENTS

FIELD OF THE INVENTION

[0001] The present invention relates to an implant, preferably for implantation in humans, which implant comprises flexible, thread-shaped elements and is particularly suitable for replacing ruptured articular ligaments. More particularly, the present invention relates to an implant intended to be a temporary implant which disintegrates in time into fragments which are so small that they can be transported away by the blood and excreted through the kidneys.

BACKGROUND OF THE INVENTION

[0002] Every year, millions of people are affected by damage to articular ligaments and tendons. A damaged ligament can be treated by surgical intervention or by conservative therapy. In spite of the fact that leading orthopaedic experts agree that surgical intervention is to be preferred in most cases, conservative therapy remains the most frequently used alternative. A major reason for this is that existing operative techniques using existing implants are considered to be inadequate.

[0003] A common feature of all types of reconstruction is that the surgeon has to use some form of replacement material to replace the damaged tissue. The most frequently used type of replacement material is tissue of the patient himself (autograft) which the surgeon takes from other parts of the body. This tissue is often supplemented with a synthetic material as reinforcement (augmentation implant). Alternatively, use is made of only a synthetic material (prosthetic implant). Implant materials which have been tried over the last 20 years in addition to autografts are inter alia tendons from animals (xenografts), deceased humans (allografts), synthetic materials in the form of non-degradable bands (Dacron, polyethylene, polypropylene, carbon fibers, polytetrafluoroethylene), and a degradable band made of polydioxanone.

[0004] Temporary implants for implantation in humans or animals comprising flexible, thread-shaped elements are known. One such has been described in Swedish Patent No. 457,392. The implant according to this patent specification consists of a bioresorbable material and is intended to completely or partly replace a tendon, a ligament or a cruciate ligament. The implant has an elongated shape and is flexible. Its main characteristic is that the structure has longitudinal grooves or ducts intended to serve as initial growth guides for new fibrous tissue. Furthermore, a large number of bioresorbable materials are also known and used for other types of implant.

[0005] In certain cases, the synthetic non-degradable implant materials have proved to have inadequate tissue-affinity and in the majority of cases inadequate elasticity with creep or fatigue failure as a consequence.

[0006] Biological tendon tissue from the patient himself, animals or deceased humans has also not proved to be an optimum alternative. The absence of a natural blood supply means that the elasticity and the strength are already reduced after a few weeks. Moreover, there is always a risk of transmitting infection when using implants from other humans and animals. In cases where tissue is taken from other parts of the body, the patient may suffer temporary or permanent harm from the wound created at the place from where healthy tissue has been taken.

SUMMARY OF THE INVENTION

[0007] In accordance with the present invention, these and other objects have now been realized by the invention of a biodegradable porous implant which is biocompatible with humans or animals comprising a plurality of bundles of flexible threads, each of the plurality of bundles comprising a plurality of the flexible threads, and each of the plurality of flexible threads comprising from 50 to 500 filaments having a combined density of from 5 to 120 tex, each of the plurality of bundles having a predetermined twist of up to 150 revolutions per meter, and weft thread means holding together the plurality of bundles, the weft thread means having a distribution density of up to about 100 threads per cm calculated in the longitudinal direction of the flexible threads. In a preferred embodiment, each of the plurality of bundles comprises several thousand of the flexible threads.

[0008] In accordance with one embodiment of the biodegradable implants of the present invention, the flexible threads and the weft thread means comprise the same thread material.

[0009] In accordance with another embodiment of the biodegradable implants of the present invention, the flexible threads comprise linear block polymers having a molecular weight of at least $10^4$ Dalton, the linear bulk polymers comprising urea groups, urethane groups, and ester groups spaced apart a predetermined distance whereby upon hydrolysis of the flexible threads fragments are produced of a size sufficiently small to be excreted from a human body. In a preferred embodiment, the linear block polymers have a molecular weight of at least $10^5$ Dalton. Preferably, the linear block polymers include primary $NH_2$-end or OH-end groups replaceable by a monoamine, preferably butylamine or ethylamine.

[0010] In accordance with another embodiment of the biodegradable implants of the present invention, the implants include a central isotropic portion for absorbing constant loading and a movable outer portion for absorbing forces caused by extension or compression.

[0011] In accordance with another embodiment of the biodegradable implants of the present invention, the implants comprise an articular ligament implant or tendon implant.

[0012] It has long been desired to produce a resorbable implant without the abovementioned shortcomings and, according to the present invention, a porous, in humans or animals biodegradable, biocompatible implant for implantation in humans or animals comprising flexible, thread-shaped elements has been produced, in which the thread-shaped elements consist of a number of thread bundles containing up to several thousand threads which in turn contain 50 to 500 filaments with a combined density of 5 to 120 tex, the thread bundles having a twist of from 0 to 150 revolutions/meter and being held together by weft threads with a distribution density of a few threads per cm up to roughly 100 threads per cm calculated in the longitudinal direction of the thread-shaped element.

[0013] According to the present invention, it is suitable for the weft threads to consist of the same type of thread as the other threads in the thread-shaped element.

[0014] According to the present invention, the material in the threads should consist of a linear block polymer with a molecular weight of at least $10^4$ Dalton, preferably at least $10^5$ Dalton, comprising urea groups and urethane groups and also ester groups at such a distance from one another that, after hydrolysis of the same, fragments arise which are so small that they can be excreted from a human body, and also comprising primary $NH_2$-end groups and/or OH-end groups which can be replaced by, for example, monoamines such as butylamine or ethylamine.

[0015] The implant according to the present invention preferably consists of a central isotropic part for essentially absorbing constant loading, and a movable outer part for absorbing forces caused by extension and/or compression.

[0016] According to the present invention, the implant consists of an articular ligament implant or tendon implant.

BRIEF DESCRIPTION OF THE FIGURE

[0017] The present invention will be described in greater detail below with reference to the following detailed description, which, in turn, refers to the drawing, in which:

[0018] The Figure is a side, perspective view of one embodiment of an implant according to the present invention.

DETAILED DESCRIPTION

[0019] The figure shows a section of an articular ligament according to the present invention comprising only three thread bundles 1. The articular ligament usually consists of, for example, 1 to 500 such thread bundles, depending on where in the body it is to be used. As can be seen from the figure, these thread bundles 1 are lightly twisted with a twist of 10 to 150 revolutions per meter. This twist is primarily intended to prevent entanglement of filaments and/or threads across the width of the ligament.

[0020] The thread bundles 1 consist of up to several thousand threads 2 which in turn each contain 50 to 500 filaments. Each thread bundle can thus contain a very large number of filaments from a few hundred up to several hundred thousand.

[0021] In order for the thread bundles 1 to be held together, they are bound together by weft threads 3 which are preferably applied in a weaving machine and using the simplest possible type of weave, usually a plain weave. The distance between the weft threads can vary from a distribution density of a few threads per cm up to roughly 100 threads per cm, depending on the desired firmness of the ligament. The closer the threads lie, the more rigid and firm the ligament. The weft threads 3 suitably consist of the same material as the threads 2 in the thread bundles 1.

[0022] The thread bundles 2 do not have to have the same thickness throughout the ligament. If the implant is to be used as an articular ligament in a knee, for example, it is suitable for the thread bundles in the central part of the ligament to be made somewhat thicker than the outer parts so that loads across the ligament are as much like the autologous ligament as possible, that is to say with a central isotropic part which is essentially to absorb constant loading while the outer thread bundles can be more easily movable so as to be capable of freely absorbing the forces caused by extension and/or compression which arise, for example, during bending and torsion of a knee joint. The thread bundles can therefore slide somewhat in relation to one another.

[0023] The construction according to the present invention is loose, which affords an enhanced possibility of immigration of connective tissue cells into the ligament. The strength and the elasticity of the construction can be adapted, which makes it possible for the patient to be active soon after an operation, development of the correct type of collagen fiber thus being stimulated. Adaptation is effected by varying the number of thread bundles, the number of threads in the thread bundles and the density of the weft threads. The strength in an articular ligament according to the present invention can vary between 50 MPa and 500 MPa. The modulus of elasticity in an articular ligament according to the present invention can vary between 100 MPa and 1500 MPa.

[0024] The construction according to the present invention affords a number of advantages in comparison with previously known implants, namely maximum utilization of the thread strength as a result of a small filament angle in the fibre strand (small cosine $\phi$ factor), and adapted but limited mobility between the fibre strands, a loose construction to enhance the possibility of immigration of the body's own connective tissue cells, and adapted strength and elasticity.

[0025] The material in the filaments and the threads should be degradable in the body and preferably consists of those linear block polymers comprising urea groups and urethane groups which comprise hydrolyzable ester groups and are described in Swedish Patent No. 505,703. Other materials which are degradable and resorbable in the body can also be used.

[0026] Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims